United States Patent [19]

Wissner et al.

[11] Patent Number: 4,764,498

[45] Date of Patent: Aug. 16, 1988

[54] SILICA-CONTAINING SHAPED ARTICLES AND A PROCESS FOR THEIR PREPARATION

[75] Inventors: Adolf Wissner; Josef Haydn, both of Leverkusen; Udo Birkenstock, Ratingen, all of Fed. Rep. of Germany

[73] Assignee: Bayer Aktiengesellschaft, Leverkusen, Fed. Rep. of Germany

[21] Appl. No.: 791,890

[22] Filed: Oct. 28, 1985

Related U.S. Application Data

[62] Division of Ser. No. 453,027, Dec. 27, 1982.

[30] Foreign Application Priority Data

Jan. 9, 1982 [DE] Fed. Rep. of Germany ....... 3200483

[51] Int. Cl.[4] .......................... B01J 20/10; B01J 21/14
[52] U.S. Cl. .................................... 502/251; 502/232; 502/407; 502/439
[58] Field of Search ............... 502/232, 407, 410, 439, 502/240, 251

[56] References Cited

U.S. PATENT DOCUMENTS

| | | | |
|---|---|---|---|
| 661,056 | 11/1900 | Jolles et al. ......................... | 502/410 |
| 2,057,414 | 10/1936 | Briggs et al. ........................ | 502/407 |
| 2,261,517 | 11/1941 | Greger ................................ | 502/407 |
| 2,921,035 | 1/1960 | Houdry .............................. | 502/232 |
| 2,941,958 | 6/1960 | Connor, Jr. et al. ............... | 502/232 |
| 3,381,688 | 5/1968 | Satas ................................... | 502/407 |
| 3,993,597 | 11/1976 | Stiles .................................. | 502/240 |
| 4,608,361 | 8/1986 | Kanamori et al. ................. | 502/232 |

FOREIGN PATENT DOCUMENTS 2625705 12/1976 Fed. Rep. of Germany ...... 502/232
343441 2/1931 United Kingdom ............... 502/232

*Primary Examiner*—Carl F. Dees
*Attorney, Agent, or Firm*—Sprung Horn Kramer & Woods

[57] ABSTRACT

In the new shaped articles a hollow space or a lumpy inorganic base material is surrounded by a porous silica-containing layer. They can be prepared by applying silica sol or a mixture containing water, silica sol and/or waterglass and, if appropriate, finely pulverulent water-insoluble silica and/or porosity producing agents to a lumpy base material, and, if use is made of organic base materials, then removing these organic base materials by heating. The new shaped articles can be used as support material for catalysts or, if the layer containing the porous silica contains catalytically active substances, as catalysts.

26 Claims, No Drawings

SILICA-CONTAINING SHAPED ARTICLES AND A PROCESS FOR THEIR PREPARATION

This is a division of application Ser. No. 453,027, filed 12/27/82, now pending.

The present invention relates to new silica-containing shaped articles, a process for their preparation, and their use as catalysts and support materials for catalysts.

Silica-containing shaped articles are widely used as catalysts and as support materials for catalysts. A large group of shaped articles of this type is formed by homogeneous silica materials, for example spheres having diameters within the range of 2 to 5 mm or extruded profiles, and is prepared by, for example, pouring silica hydrosol into organic liquids not miscible with water or by mechanical shaping (see, for example, German Auslegeschrift No. 1,197,851 and the following company leaflets: Kali-Chemie Katalysatoren [Catalysts], 1980; Süd-Chemie K-Katalysatoren [K Catalysts], 1973; and BASF Katalysatoren Verkaufsprogramm [List of catalysts for sale], 1967).

When directly used as catalysts or after having been coated with catalytically active materials, for example by spraying or impregnating, shaped articles of this type have the disadvantage that the catalytically active centres are distributed more or less uniformly in the entire shaped article (see, for example, U.S. Pat. No. 3,743,607). The result of this feature is that reactants and reaction products can be retained in the shaped article and initiate the formation of undesirable by-products and secondary reactions (see, for example, Suter, Phthalsäureanhydrid und seine Verwendung [Phthalic anhydride and its use], published by Steinkopf, Darmstadt, page 20 (1972)). Moreover, by-products and catalyst poisons in the interior of the shaped article can increase in concentration and hence be removable by means of customary regenerating methods only with extreme difficulty or not at all. These adverse effects arise to a particularly pronounced extent when the shaped articles are porous throughout their entirety.

Attempts have therefore been already made to prepare catalysts which, in their interior, are almost free of pores and/or catalytically active centres. An example of such a catalyst is the catalyst described in U.S. Pat. No. 1,987,506 and in which 4 to 6 mm large grains of a slightly porous or poreless support, such as corundum or silicon carbide, are coated with vanadium pentoxide. To improve on this type of catalyst a mixture of vanadium pentoxide and titanium dioxide is applied to inert, smooth spheres made of porcelain, steatite or quartz (see Chemie-Ingenieur-Technik 4, 967 to 970 (1969)). In these catalysts the catalytically active constitutent, owing to a low melting point and the tendency to form a glass, is particularly suitable for being applied as a surface coating. Catalysts are also known which are based on the same preparation principle and in which catalytically active constituents other than vanadium pentoxide are applied to a support either in pure form or mixed with titanium dioxide. All such catalysts containing titanium dioxide have the disadvantage that they, together with other acidic catalyst constituents, acidic reactants or reactants containing acidic compounds, have inadequate mechanical stability.

For example, German Offenlegungsschrift 2,909,670 describes a process in which catalytically active substances, for example molybdenum, vanadium, tungsten and/or copper are sprayed as oxide mixtures in the form of an aqueous suspension onto inert supports, for example silicon dioxide or silicates. In this process, the temperature of the support must be below 100° C., the support must be moistened before the spraying step, a heated inert gas must be supplied and care must be taken that the water content of the support is always larger than that of the resulting coating. In all cases a catalyst is formed, the external parts of which are not porous.

German Offenlegungsschrift 2,716,154 describes the preparation of a catalyst in which a porous silicon dioxide support is coated in a special application process in such a way with palladium and gold that these catalytically active constituents are deposited in a surface layer which extends from the surface by less than 0.5 mm. However, this application method is very involved and not generally utilisable and produces catalysts which, after a treatment with alkali metal acetate, consist of active silica material and catalytically active substances also in their interior.

Silica-containing shaped articles have now been found which are characterised in that a hollow space or a lumpy inorganic base material is surrounded by a porous silica-containing layer.

Insofar as, in the shaped articles according to the invention, a lumpy inorganic base material is surrounded by a porous silica-containing layer, the inorganic base material can consist of a very wide variety of materials which can be non-porous, slightly porous or very porous and are sufficiently strong and inert. Examples which may be mentioned are silicon dioxide and silicates, such as sodium aluminosilicates, magnesium silicates (for example steatites), zirconium silicates, silicate glasses, quartz, calcium zirconiosilicates and aluminum silicates; alumina and products containing alumina, such as corundum, α-alumina, γ-alumina, calcium aluminate and spinels, such as lithium spinels; other oxidic materials, such as titanium dioxide, zirconium dioxide, thorium dioxide, magnesium oxide and zinc oxide; metallic materials, such as steels, iron and copper; stone, such as granite, basalt, natural iron oxides and pumice; materials customarily used as packing media for columns, such as Raschig rings, Berl saddles and ceramic bodies made of, for example, glass, porcelain or clay; and other inorganic materials such as carbides, for example silicon carbide, carbonates, for example calcium carbonate as well as slags, ashes, carbons and expanded clay.

The inorganic base material preferably consists of materials of low absorbency and having a low BET surface area. The absorbency is preferably less than 10, particularly preferably less than 5, g of water per 100 g, and the BET surface area is preferably below 5 m$^2$/g. If inorganic base materials having a higher absorbency and/or a higher BET surface area are given, it is advantageous to arrange for there to be another layer between the inorganic base material and the layer containing porous silica which other layer reduces the porosity of the inorganic base material at its surface to such an extent that the preferable ranges are given at the surface for the absorbency and the BET surface area. This point will be described in more detail further on. Moreover, the inorganic base material preferably consists of silicates, in particular magnesium silicates in the form of steatites, silicon dioxide, aluminas, steels, iron, smelted ashes, smelted slags or packing media.

The crystal structure of the inorganic base material is of no particular importance. The inorganic base materials can be crystalline or amorphous.

The shape and particle size of the lumpy inorganic base material is likewise of no particular importance. The inorganic base materials can be, for example, tableted, grainy or otherwise lumpy and be extrudates, spheres, collared spheres, granules, tubelets, rodlets, cylinders, grinding base and other optionally shaped articles, for example rings. In particular metallic materials can also be in the form of wires, wire nets, bolts, nuts and other shaped hardware. The particles of the inorganic base materials preferably have dimensions within the range of 0.5 to 15 mm. Spheres, granules and mill base having a mean diameter within the range of 0.5 to 15 mm are particularly preferable, and spheres, granules and mill base having a mean diameter of 2 to 10 mm are very particularly preferable. The inorganic base material can also consist of particles of various types, for example steatite and slags, and of differing shape, for example spheres and mill base.

In shaped articles according to the invention either one of the inorganic base materials described above or a hollow space is surrounded by a layer containing porous silica. The thickness of this layer can vary within wide limits, for example from 10 to 3,000 μm. The mean thickness of this layer is preferably 20 to 2,000 μm. The layer thickness can vary from particle to particle and also within a particle; the latter feature applies in particular when irregularly shaped inorganic base materials are present such as, for example, in the case of ash or mill base.

In particular embodiment of the invention, the layer containing porous silica also contains catalytically active substances or precursors thereof. These catalytically active substances or precursors thereof can be of the most diverse type. They can be, for example, metals, metal compounds, non-metals, non-metal compounds, complex compounds, ion exchange materials, carbons and/or zeolites. Examples of what is suitable for this purpose are elements and/or compounds of elements of the 1st to 6th main group and/or of the 1st to 8th secondary group of the periodic system as well as compounds of rare earths and/or actinides. The following elements may be mentioned as particular examples: lithium, sodium, potassium, rubidium, caesium, beryllium, magnesium, calcium, strontium, barium, titanium, zirconium, hafnium, vanadium, niobium, tantalum, chromium, molybdenum, tungsten, manganese, rhenium, iron, ruthenium, osmium, cobalt, iridium, rhodium, nickel, palladium, platinum, copper, silver, gold, zinc, cadmium, mercury, boron, aluminium, carbon, silicon, tin, lead, phosphorus, arsenic, antimony, bismuth, cerium, scandium, yttrium, gallium, thallium, germanium, samarium, thorium and/or uranium. These elements can be present as such or in the form of compounds, but, of course, all those elements and compounds are excluded which are not sufficiently stable. The porous layer containing silica can also contain metals of the Raney type, for example Raney nickel, Raney iron and/or Raney cobalt, or the precursors thereof, for example finely divided Raney alloys.

Examples of possible compounds and complex compounds are salts and/or complex compounds of the above-mentioned elements, preferably oxygen-containing compounds such as oxides, hydroxides, sulphates, carbonates, carboxylates (for example acetates), nitrates, phosphates, silicates, borates and aluminates, but also cyanides, fluorides, chlorides, bromides, phthalocyanines, acetylacetonates and other complex compounds. Examples of suitable compounds are listed in A. F. Wells, Structural Inorganic Chemistry, 3rd edition, Oxford at the Clarendon Press (1967) and in D. Brown, J. H. Canterford and R. Coltan, Halides of the Transition Elements, Volume 1 to 3, John Wiley and Sons, London (1968).

Preferable possible compounds are lithium sulphate, sodium sulphate, sodium acetate, potassium sulphate, potassium acetate, rubidium sulphate, caesium sulphate, lithium carbonate, sodium carbonate, potassium carbonate, rubidium carbonate, caesium carbonate, and the corresponding bicarbonates, lithium oxide, sodium oxide, potassium oxide, caesium oxide, rubidium oxide, beryllium oxide, magnesium oxide, calcium oxide, strontium oxide, magnesium carbonate, calcium carbonate, strontium carbonate and the corresponding bicarbontes, vanadium pentoxide, vanadyl sulphate, vanadyl oxalate, chromium trioxide, molybdenum trioxide, tungsten trioxide, manganese oxide, manganese dioxide, rhenium oxide, iron(II) oxide, iron(III) oxide, iron-(II/III) oxide, ruthenium dioxide, cobalt(II) oxide, cobalt(II/III) oxide, nickel oxide, copper oxide, zinc oxide, boron oxide, aluminium oxide, tin dioxide, lead monoxide, lead dioxide, lead(II/IV) oxide, phosphorus pentoxide, cerium dioxide, antimony trioxide, antimony pentoxide, arsenic acid, arsenic trioxide, beryllium nitrate, lead nitrate, lead acetate, cadmium nitrate, cadmium sulphate, cerium(III) nitrate, cerium(IV) sulphate, chromium(III) nitrate, iron(III) nitrate, iron(II) sulphate, iron(III) sulphate, potassium dichromate, potassium chromate, potassium hexacyanoferrate(II), potassium hexacyanoferrate(III), potassium tetrahydroxyantimonate, dipotassium hydrogenphosphate, cobalt nitrate, copper nitrate, copper sulphate, lanthanum nitrate, manganese(II) nitrate, sodium arsenate, sodium molybdate, sodium vanadate, sodium tungstenate, nickel nitrate, nickel sulphate, mercury(II) nitrate, silver nitrate, thallium nitrate, thorium(IV) nitrate, uranyl nitrate, bismuth nitrate, zinc nitrate, zirconyl chloride, hexachloroplatinic acid, potassium hexachloroplatinate, sodium tetrachloropalladate, palladium chloride, palladium bromide, palladium iodide, potassium hexachloropalladinate, palladium acetate, palladium nitrate, palladium sulphate, palladiumdiamine dichloride, rhodium trichloride, rhodium trinitrate, hexachloroiridic acid, iridium trichloride, ruthenium trichloride, bismuth trichloride, chromium trichloride, samarium trichloride and/or niobium oxychloride, and phosphoric acid, hydrophosphates, dihydrogenphosphates, pyrophosphates, for example vanadyl phosphates, vanadyl pyrophosphates, iron phosphates, iron pyrophosphates and copper phosphates.

Carbons, zeolites, ion exchanger materials, aluminas and silicas are all of particular interest.

The carbons are preferably pulverulent, carbon-containing systems, for example activated carbons as described in "Lurgi Schnellinformation (T 1091/8.75), Pulverförmige Aktivkohlen [Pulverulent activated carbons]" Suitable activated carbons have, for example, the composition: carbon 83 to 93% by weight, hydrogen 1 to 3% by weight, oxygen 0.2 to 10% by weight, nitrogen traces, sulphur traces, and they contain ash to make up to 100% by weight and have surface areas of up to 1,500 m$^2$/g and larger. They have, for example, a particle size of less than 1 mm, preferably a fineness of grind of about 20% by weight above 75 μm.

The zeolites can be of the naturally occuring or synthetically prepared type, for example systems consisting of silica and alumina in conjunction with alkali metal or alkaline earth metal oxides. Suitable zeolites are extensively described in R. M. Barrer, Molecular Sieves Society of Chemical Industry, London, page 39 (1968) and in the guide of Bayer AG "Bayer-Zeolith", edition of 1st January 1978. Suitable zeolites have, for example, the following characteristics: pore width 3 to 9 Å, screen size 1 to 6 mm and bulk density 600 to 750 g/l and they are preferably fine powders having a particle size of considerably less than 1 mm.

The ion exchange materials can be synthetic resins which, owing to their chemical make-up and to a porous, water-permeable structure, are extremely reactive in the sense of bonding foreign ions via cation or anion exchange. Examples of suitable ion exchange materials are described in the guide of Bayer AG with the title "Lewatit ®/Lewasorb ®", product information, edition January 1981. Not only cation but also anion exchange materials, for example the types strongly acidic gel-like Na or H form, strongly acidic macroporous Na form, weakly acidic macroporous H form, strongly basic gel-like Cl or OH form, strongly basic macroporous Cl form, weakly basic macroporous Cl form and weakly basic macroporous OH or OH/Cl form, are suitable. The particle size of the ion exchange materials should ideally be less than 1 mm, preferably less than 0.5 mm.

The aluminas can be all intermediate stages, from aluminium oxide hydrates to pure aluminium oxide, as described, for example, in the company leaflets issued by Rhone-Poulenc with the titles "Activated Alumina" and "Alumina catalyst carriers Spheralite ®". For example aluminas containing more than 95% by weight of $Al_2O_3$ are possible. However, the aluminas can also have lower $Al_2O_3$ contents. Preferably, possible alumina is a pulverulent material having a particle size of less than 1 mm, preferably below 0.5 mm.

Possible silicas are the fine-porous, water-insoluble silicas dsecribed below.

The present invention also relates to a process for preparing silica-containing shaped articles of the type described above, which is characterised in that silica sol or a mixture containing water, silica sol and/or waterglass and, if appropriate, finely pulverulent water-insoluble silica and/or porosity-producing agents are applied to a lumpy base material, the temperature of which is, at the start of the application of the silica sol or of the mixture, below the softening point of the base material and, as the application of the silica sol or of the mixture proceeds, above the boiling temperature of water, the silica sol or the mixture being added in such a way that the water evaporates rapidly, and the water content of the base material is always less than 5% by weight, and, if use is made of organic base materials, these organic base materials are then removed by heating to temperatures within a range of 200° to 1,300° C.

Inorganic and organic materials are suitable for use as base material for preparing shaped articles according to the invention. Suitable inorganic base materials are those described above, but care should be taken to ensure their average residual moisture content at the start of and during the application of the silica sol or of the mixture is kept very low, that is always below 5% by weight, preferably significantly lower.

Suitable organic base materials are those which are non-porous, hardly porous or highly porous, sufficiently firm, and sparingly soluble in water. Preferred are solid polymeric materials, for example polystyrenes, polycarbonates, polyolefines, cellulose, cellulose derivatives, polyurethanes, polyacrylonitriles, acrylonitrile-styrene-butadiene copolymers, polyesters, polyvinyl chlorides, polyfluoroethylenes, polyfluoroethylene derivatives, polyamides, epoxy resins or polycondensates, for example of phenol and formaldehyde. Preferably the organic base material consists of non-porous materials which have a softening point above 60° C. The shape and size of organic base materials can correspond to those of the inorganic base materials described above. Suitable organic base materials are in general hydrophobic, so that in general their water content before or during the application of the mixture need not be particularly watched.

The organic base materials are removed by heating after the silica sol or the mixture has been applied. This heating step generates hollow spaces which are surrounded by a layer containing porous silica.

The base material used can also be a mixture of various organic base materials, for example polystyrene and polycarbonate, or even a mixture of inorganic and organic base materials, for example steatite and polycarbonate. It is also possible to use organic base materials which contain inorganic constituents, for example glass fibre reinforced polymers.

Examples of what can be applied to the base material are:
only silica sol or
mixtures which, in addition to water, contain the following constituents:
(a) silica sol,
(b) waterglass,
(c) silica sol and waterglass in any mixing ratios,
(d) 10 to 90% by weight of silica sol and an amount to add up to 100% by weight of finely pulverulent, water-insoluble silica, in each case calculated and relative to anhydrous $SiO_2$,
(e) 10 to 60% by weight of waterglass and an amount to add up to 100% by weight of finely pulverulent, water-insoluble silica, in each case calculated and relative to anhydrous $SiO_2$,
(f) 10 to 90% by weight of silica sol and waterglass, the waterglass content being at most 60% by weight of the mixture, and an amount to add up to 100% by weight of finely pulverulent, water-insoluble silica, in each case calculated and relative to anhydrous $SiO_2$.

Mixtures which contain only waterglass as the silica-type component are generally only used when, for example when using strongly porous base materials or those having very smooth surfaces, it is intended to produce a first layer to reduce the porosity and/or improve the bonding and one or more layers containing further or other silica-type components are applied thereafter. When silica sol is solely used and in the case of all other water-containing mixtures, it is of no particular importance to which type of base material they are applied, whether they are used to produce single or multiple coatings and whether the layer produced is to be followed by one or more further layers. Silica sol and mixtures as described under (d), (e) and (f) are preferably used, if appropriate together with porosity-producing agents.

If water is used for preparing the components or component mixtures to be applied, a very wide variety of organic solvents can, if appropriate, be added to the water as an auxiliary medium, but it is not always necessary to establish a homogeneous liquid phase. Examples of possible organic solvents are aliphatic, cycloaliphatic or aromatic as well as heterocyclic compounds which can also be substituted. Suitable aliphatic hydrocarbons are straight-chain or branched hydrocarbons having 1–12, preferably 5–8, hydrocarbon atoms. Possible cyclic hydrocarbons are those which have 5–7, preferably 6, carbon atoms in the ring system. Possible heterocyclic compounds are those which have 5–7 and preferably 6, atoms in the ring system. Preferable suitable heterocyclic compounds are 5- and 6-membered systems which can contain oxygen and/or nitrogen as the heteroatom.

The solvents added can have substituents, such as halogen atoms, for example fluorine, chlorine or bromine, hydroxyl, amino, sulphonic acid or carboxyl groups and esters thereof, $C_1$–$C_4$-alkoxy groups and $C_1$–$C_{12}$-alkyl radicals. Particularly preferable organis solvents are hydrocarbons such as hexane, cyclohexane, benzene, toluene and xylene, alcohols such as methanol, ethanol, propanol, isopropanol, butanol, amyl alcohol, ethylene glycol, glycerol and cyclohexanol, ethers, such as ethylene glycol monoethyl ether, ethylene glycol diethyl ether, ethylene glycol monotolyl ether and triethylglycol methyl ether, ketones, such as acetone, amines, such as ethylamine, cyclohexylamine and ethylenediamine, phenols, such as phenol, 3-acetoxyphenol, resorcinol and pyrocatechol, as well as blends and mixtures of these compounds in the most diverse compositions.

If organic base materials and organic solvents are used, care should be taken to ensure that only those organic solvents are used in which the particular organic base material is insoluble or only sparingly soluble.

In particular cases it is also possible to use mixtures in which the liquid medium contains only very small proportions of water.

Any silica-containing materials or mixtures to be applied to the base material can optionally contain in addition one or more porosity-producing agents, for example 0 to 100, preferably 0 to 50, % by weight, relative to all silica constituents present and calculated as anhydrous $SiO_2$.

The silica sol used can be aqueous, colloidal, silica solutions having the most diverse properties and described, for example, in the guide Bayer-Anorganika, Silica Sol, Order No. AC 10006 e of the 1st Feb. 1973. The silica sol preferably contains 15 to 45% by weight of $SiO_2$ and below 0.5% by weight of $Na_2O$ and has a pH value within a range of 3.4 to 10, a density within a range of 1.09 to 1.33 g/cm$^3$ and a particle size within a range of 7 to 30 μm. Suitable silica sols are commercially available.

Aqueous solutions of alkali metal silicates, in particular commercially available alkali metal silicate solutions obtainable under the labels Kaliwasserglas [potash waterglass] and Natronwasserglas (sodium waterglass) and containing up to 30% by weight of $SiO_2$ are possible for use as waterglass. Other suitable waterglass types are those described in Hollemann-Wiberg, Lehrbuch der anorganischen Chemie [Textbook of inorganic chemistry] 71st to 80th edition, published by Walter de Gruyter, Berlin, page 497 (1971). However, solid alkali metal metasilicates, for example potassium metasilicate, which contain up to 75% by weight of $SiO_2$ can also be used as waterglass. Silica sol can be used on its own, but it is also possible to use a mixture of water and silica sol, mixtures of water and waterglass or mixtures of water, silica sol and waterglass.

Examples of what can be used as finely pulverulent water-insoluble silica are the most diverse amorphous or crystalline silicas, with the primary particle size being, for example, 1 to 200 nm and the agglomerate size being, for example, 0.5 to 100 μm.

Such silicas are commercially available and described, for example, in H. Ferch, Chemie-Ingenieur-Technik 48, pages 922 et seq. (1976). They are in general synthetic silicas, which can be prepared in various ways, for example from silicon tetrachloride, hydrogen and oxygen by the flame hydrolysis method or from quartz and coke by the arc method. Of particular importance are the silicas prepared by the so-called "wet process" and where silica is obtained from waterglass and acid by precipitation and subsequent drying or from sand and chalk by the hydrothermal process. All silica products obtainable by this process are commercially available.

The finely pulverulent, water-insoluble silica preferably has the following characteristics: specific surface area 30 to 2,000 m$^2$/g, primary particle size 3 to 100 nm, agglomerate size 1 to 40 um, density about 2.0 g/cm$^3$, compacted volume (according to DIN 53,194) 100 to 2,000 ml/100 g, loss on drying (according to DIN 53,198) 3 to 7%, loss on ignition (according to DIN 55,921) 3 to 15%. pH value (according to DIN 53,200) 2 to 9, predominant pore diameter above 200 Å and $SiO_2$ content (relative to dry substance) above 93%.

The finely pulverulent, water-insoluble silicas to be used can contain small amounts of contaminants, for example up to 1% by weight of aluminium (calculated as $Al_2O_3$), up to 0.5% by weight of iron (calculated as $Fe_2O_3$) and up to 2% by weight of sulphur (calculated as $SO_3$), in each case relative to the dry weight of the silica.

The silica preferably contains less than 0.5% by weight of aluminium, less than 0.1% by weight of iron and less than 1% by weight of sulphur, in each case calculated and relative to the dry weight of the silica.

Kieselguhr can also be used as finely pulverulent, water-insoluble silica.

Kieselguhr can be the natural product commercially available under this label and described, for example, in Rompp's Chemielexikon [Römpp's Chemistry Dictionary], volume H to L, 7th edition, Franckh'sche Verlagshandlung W. Keller & Co., Stuttgart, page 1770 (1973). The natural product is preferably a fine-grained, light powder which contains 70 to 90% by weight of amorphous silica, 3 to 12% by weight of water and small impurities of oxides of other elements, for example of aluminium and of iron.

The silica sol and the mixtures containing water, silica sol and/or waterglass, either of which may contain added amounts of solvents and/or finely pulverulent, water-insoluble silica, do not necessarily require the addition of porosity-producing agents. Particularly when larger amounts of Kieselguhr are present, porosity-producing agents can be dispensed with, since kieselguhr exerts a loosening action on the silica-containing layer. However, one or more porosity-producing agents are preferably added regardless of the presence of kieselguhr.

Suitable porosity-producing agents are the activated carbons, carbon blacks and graphite previously described and materials which can be decomposed thermally in an easy and largely residue-free manner. Such porosity-producing agents are in themselves known. Possible examples are organic and/or inorganic materials, such as ammonium salts, aliphatic alcohols of the empirical formula $C_nH_{2n+2}O$, aliphatic dihydroxy, trihydroxy and polyhydroxy compounds, aliphatic carboxylic acids of the empirical formula $C_nH_{2n}O_2$ (also in the form of their salts, esters and other derivatives), aliphatic dicarboxylic acids of the empirical formula $C_nH_{2n-2}O_4$, higher aliphatic carboxylic acids and sugars (also in the form of derivatives and polysaccharides), and readily and completely decomposable polymers, such as polystyrene.

Examples of single compounds or materials suitable for use as porosity-producing agents are ammonium carbonate, ammonium hydrogencarbonate, ammonium nitrate, ammonium acetate, ammonium formate, ammonium oxalate, ethylene glycol, glycerol, sugar alcohols, acetic acid, propionic acid, oxalic acid, sodium acetate, malonic acid, ascorbic acid, tartaric acid, citric acid, glucose, sucrose, starch, cellulose and graphite.

The porosity-producing agents preferably used are ammonium salts, oxalic acid and graphite.

The graphite can be natural or synthetic graphite. The graphite can contain, for example, 70 to 90% by weight of carbon and 10 to 30% by weight of ash and have a particle size which is essentially below 0.1 mm. The ash fractions in general essentially contain silica and also alkali metal and alkaline earth metal oxides as well as, if appropriate, oxides of iron and/or of other transition metals.

In the mass to be applied to the base material the fractions of silica sol, water and/or waterglass and, if appropriate, finely pulverulent water-insoluble silica and/or porosity-producing agents can vary within wide limits. If all silica constituents present are calculated as anhydrous $SiO_2$, the content of silica sol, relative to anhydrous $SiO_2$, can be, for example, 10 to 100% by weight, provided no waterglass is used. If silica sol and waterglass are used, their total content, calculating all silica constituents present as anhydrous $SiO_2$, can be, for example, 20 to 80% by weight, with the waterglass fraction thereof preferably not exceeding 55% by weight. The mass to be applied to the base material should contain enough water, if appropriate together with added solvents, that the mass is highly mobile. The mass can contain, for example, relative to all silica constituents present and calculated as anhydrous $SiO_2$, 30 to 95% by weight, preferably 40 to 85% by weight, of water.

By varying the composition of the mass to be applied to the base material within the scope of the limits indicated, the physical parameters of the silica-containing layer formed can be affected, namely, for example, the pore volume, the (mean) pore diameter, the pore radius distribution, the porosity, the apparent density, the true density, the fraction of coarse pores, the fraction of fine pores, the absorbency, the abrasion resistance, the mechanical strength, the specific (BET) surface area, the specific active surface area and the surface acidity.

This mass can be applied to the base material by methods which are in themselves known, for example by means of casting, spraying or granulating methods, in which the particles of the base material are preferably in permanent intrinsic motion and in which uniform and constant mixing is aimed at. In applying the mass to the base material it is essential, on the one hand, that the temperature of the base material at the start of the application of the silica sol or of the mixture is below the softening point of the base material, and, on the other hand, that the water applied to the base material together with the silica sol or the mixture evaporates rapidly.

If use is made of inorganic base materials, which in general have high softening or melting points, their temperature is therefore preferably kept above the boiling temperature of water, that is above 100° C. when working under atmospheric pressure, throughout the entire application of silica sol or of the mixtures described above. Preferable temperatures are within a range of 105° to 800° C., in particular within a range of 110° to 400° C., more particularly within a range of 110° to 300° C.

Organic base materials can have softening points below the boiling temperature of water. If organic base materials are used, their temperature at the start of the application of silica sol or of the mixtures described above is therefore kept below their softening point, even if as a result the temperature is below the boiling temperature of water. The application of silica sol or of the mixtures described above must then if necessary be carried out more slowly to ensure that the water still evaporates rapidly. Immediately after the organic base material has been coated with a silica-containing layer, the temperature of the base material is raised to values above the boiling temperature of water and the application of silica sol or of mixtures is completed at temperatures above the boiling temperature of water. The maximum temperature which can be used in this case depends on the nature of the organic base material. In general this heating is carried out at temperatures within a range of 105° to 300° C., preferably 110° to 220° C. Organic base materials which have a softening point above about 110° C. are treated with silica sol or the mixture preferably throughout at temperatures above the boiling temperature of water.

If the mass to be applied (silica sol or one of the mixtures described above) contains in addition to water significant amounts of solvents having a higher boiling point than water, the temperature of the base material is preferably chosen to be higher than the boiling point of the solvent having the highest boiling point. Care must also be taken that the particles of the base material have a residual moisture content of less than 5% by weight, preferably less than 1% by weight, before the application process.

If a spraying method is used to apply the mass to the base material, it is possible, for example, initially to introduce the base material into a heatable coating drum and to apply the mass to be applied by means of nozzles, for example cone nozzles, hollow-cone nozzles, dusting nozzles, one-material nozzles or multi-material nozzles. If a casting method is used, the mass to be applied can be, for example, added dropwise to the moving base material. In granulating methods, for example, the base material and a finely divided, solid catalytically active substance or a precursor thereof are granulated with the aid of silica sol or one of the mixtures described above. Spraying methods are preferably used.

The temperature of the mass to be applied is in general not critical. However, the temperature should not be so high as to evaporate significant amounts of water already before the application to the base material. Suitable temperatures are therefore for example those within a range of 10° to 50° C.

It is essential that the mass to be applied is applied to the base material in such a way that the water container in the mass to be applied is rapidly evaporated. The water content of the base material and of silica which may have already been applied to the inorganic base material must always be below 5% by weight. The water content should preferably always be below 1% by weight. In this way firm adhesion of the layer applied is obtained, in particular when using inorganic base materials.

In applying the mass to an inorganic base material the procedure used may be, for example, that the base material is heated to about 200° to 250° C. in a heatable coating drum and is then sprayed with the silica-containing mass until the temperature of the charge has fallen to about 105° to 150° C., and the charge is then heated up again to about 200° to 250° C. and newly sprayed. When strongly porous inorganic base materials are used the spraying is advantageously carried out at temperatures within a range of 250° to 300° C. This measure can minimise as far as possible the extent to which the silica-containing mass penetrates into the inorganic base material. When using strongly porous inorganic base materials the use of elevated temperatures can also be necessitated by the fact that otherwise the limits indicated above for the water content cannot be adhered to.

The silica-containing layer can be applied to an organic base material by, for example, heating the base material in a heatable coating drum to a temperature which is about 5° to 15° C. below the softening point of the base material. If this step has to be carried out at temperatures below 100° C., the silica-containing mass is sprayed on only very briefly, the water is allowed to evaporate, and the charge is heated back up to the starting temperature and sprayed again with the silica-containing mass. In this method, the temperature of the charge should preferably not drop below 60° C. As soon as sufficient silica-containing mass has deposited on the organic base material for this base material to withstand heating to temperatures above 100° C. without deformation, the spraying is carried out at temperatures of 100° C., for example at temperatures within a range of 110° to 220° C. If the softening point of the organic base material is above 110° C., application of the silica-containing mass may be carried out from the start in the way described above for the use of inorganic base materials, without, however, using temperatures so high that the base material deforms. The maximum temperature at which organic base materials can be coated depends on the nature of the organic material. In general, it is advantageous to avoid temperatures of above 220°C.

The silica-containing layer can be applied in such a way that a layer of any mean thickness, for example within a range of 10 to 3,000 $\mu$m, is formed on the base material in one operating step. However, it is also possible to proceed in such a way that, in one operating step, only a thin layer, for example within a mean thickness range of 1 to 100 $\mu$m, is formed and, if appropriate, several such layers are applied in succession. It is also possible to apply several relatively thick layers, for example those having a mean thickness range of 100 to 1,000 $\mu$m, in succession. If it is intended to apply a relatively thick layer to the base material, for example a layer having a mean thickness above 100 $\mu$m, it is in general advantageous to produce this layer in several operating steps, by superposing several relatively thin layers, for example by preparing a layer having a mean thickness of 3,000 $\mu$m either in three operating steps in each of which layer having a mean thickness of about 1,000 $\mu$m is applied or in 30 operating steps in each of which a layer having a mean thickness of about 100 $\mu$m is applied.

If the silica-containing layer is applied to the base material in several operating steps, the intervals between the individual operating steps can be arbitrarily long. It is also possible to use differently composed masses for the individual operating steps, that is to apply in succession several layers which differ in composition. For instance, it is advantageous in some cases, for example when using strongly porous base materials, or those having a very smooth surface (for example steel spheres), first to produce a layer from a mixture containing only water and silica sol and/or waterglass, whereby the porosity of the base material is reduced and/or its ability to bond further layers is improved, and then to apply one or more layers from mixtures which also contain finely pulverulent, water-insoluble silica, porosity-producing agents and, if appropriate, catalytically active substances or precursors thereof.

The thickness of the layer applied in one operating step depends essentially on the water content of the mixture to be applied and on the time during which the base material, which may already be coated with one or more silica-containing layers, is brought into contact with the mass to be applied. To apply layers of the desired thickness by varying these two parameters will not present any problems to an expert.

The mean thickness of an individual layer is preferably at least 10 $\mu$m, particularly preferably at least 20 $\mu$m.

The thickness of a layer, essentially due to the methods of application, can vary not only from particle to particle but also within a particle. However, this is generally without adverse effect on the utilisability of shaped articles prepared according to the invention as catalysts or catalyst supports. When using irregularly shaped base materials, for example mill base, ashes or slags, an approximation to the sphere shape generally takes place during application of one or more layers, since the layer applied is relatively thin at the vertices and strongly convex-shaped areas of the particles, but is relatively thick in concave-shaped regions of the particles. This feature likewise generally has no adverse influence on the utilisability of shaped articles prepared according to the invention as catalysts or catalyst supports.

After silica has been applied to an inorganic base material, the product thus obtained can, if appropriate, be thermally aftertreated. In this step, a very wide variety of temperatures can be used, for example those within a range of 200° to 1100° C. In this step preferable temperatures are within a range of 200° to 700° C., particularly preferable temperatures are within a range of 200° to 500° C., and very particularly preferable temperatures are within a range of 200° to 300° C. A thermal aftertreatment is particularly advantageous if porosity-producing agents have been used.

After silica has been applied to an organic base material a thermal aftertreatment at temperatures within a range of 200° to 1,300° C. is necessary in every case to remove the organic base material. Preferable temperatures for this step are within the range of 300° to 700° C. The general procedure followed is to remove the organic base material slowly via melting, decomposition, carbonisation and slow combustion, for example by raising the temperature from 200° to 700° C. at a rate of 30° to 70° C. per hour and then maintaining 700° C. until the entire residual carbon, recognisable by the black discoloration of the silica-containing layer, has been combusted. As a result hollow spaces are obtained which are surrounded by a layer containing porous silica. The organic base material can also be removed only when catalytically active materials, or precursors thereof, have been introduced into the silica-containing layer.

If silica-containing shaped articles which contain catalytically active substances or precursors thereof are intented to be prepared according to the invention, catalytically active substances or precursors thereof, for example of the type described above, can be applied to the base material together with the silica-containing mass. In this step, the temperatures during and after application of the layer(s) containing silica are to be controlled in such a way, if appropriate, that the catalytically active substances, or the precursors thereof, do not change in an undesirable way. However, it is also possible to proceed by first applying to the base material a mass which produces a silica-containing layer free of catalytically active substances or precursors thereof and then introducing solutions or suspensions of catalytically active substances, or precursors thereof, into the silica-containing layer, for example by customary impregnating or spraying methods.

Regardless of how the catalytically active substances or their precursors have been introduced, the most diverse aftertreatments can be performed, if appropriate, to obtain active or more active catalysts. This aftertreatment can consist, for example, of a heat treatment, a reduction or an oxidation.

The products according to the invention are distinguished by the fact that a layer of any thickness and which contains porous silica surrounds a hollow space or an optional inorganic base material. If these products are prepared as described above, solid silica-containing layers are obtained. The products according to the invention can be used as catalyst support material provided they do not contain any catalytically active centres. They can be used to prepare a very wide variety of catalysts which then all have the advantage that the catalytically active constituents are present only in the silica-containing layer, a state of affairs which yields very active and selective catalysts and wherein catalytically active material can be saved, since the interior of these catalysts is free thereof. If catalytically active substances are introduced or produced together with or after the silica-containing layer(s) has or have been applied, these advantages are likewise obtained. Compared to known catalysts, which have a $TiO_2$-containing layer, the products according to the invention have the advantages that they are porous not only at the surface but also within the applied layer(s) and that in respect of catalytically active constituents they are not restricted to those which have low melting points. The stability of the silica-containing layer to incorporated catalytically active components of acidic character and to acidic reactants has proved particularly advantageous, whereas $TiO_2$-containing layers are unstable, to the point of decomposition, under these conditions due to a chemical change of the $TiO_2$.

Silica-containing shaped articles according to the invention which contain catalytically active substances can be used as catalysts.

For example, an excellent hydrogenation catalyst can be obtained from a product according to the invention and which does not contain catalytically active constituents by applying a palladium salt solution by impregnation for example an aqueous palladium chloride solution, then drying and reducing the palladium salt. A catalyst thus prepared is particularly suitable, for example, for the hydrogenation of nitro compounds.

If products according to the invention and free of catalytically active constituents are to be impregnated with metal salt and/or noble metal salt solutions, for example one or more metals can be applied by impregnation, for example dissolved in the form of their salts. Physical parameters, such as, for example, absorbency of the support and solubility of the metal and/or noble metal salts, can necessitate several impregnations to obtain the concentration of active ingredient required in the prepared catalyst. The concentration of the metal salt and/or noble metal salt solutions is adjusted in such a way, for example, that the prepared catalyst contains 0.5 to 200 g, preferably 1 to 100 g, of one or more catalytically active components per liter of support. If the catalytically active component is a noble metal or a noble metal compound or if several catalytically active components are present in the support catalyst of which at least one is a noble metal or a noble metal compound, the content of these components can be, for example, in each case 0.5 to 100 g, preferably 1 to 50 g, particularly preferably 2 to 20 g, calculated as noble metal in elemental form, per liter of support.

For example, such a catalyst can contain 1 to 20 g, preferably 2 to 10 g, of palladium or 1 to 100 g, preferably 2 to 50 g, of a non-noble metal, or, in the case of a multi-component support catalyst, 1 to 20 g of palladium, 1 to 50 g of a first transition element and 1 to 50 g of a second transition element, in each case calculated as the metal in elemental form, per liter of support.

How this impregnating is performed in industry may be illustrated by means of the preparation of a palladium-containing $SiO_2$/steatite catalyst:

a support containing a silica layer is prepared according to the invention from steatite as the inorganic base material and impregnated commensurate with its absorbency with a metal salt solution, for example sodium palladium chloride, and dried. If necessary, the metal salt applied is first reduced to metal by known methods, for example by treatment with hydrazine hydrate solution, before a subsequent washing process and drying.

In the catalyst thus prepared the palladium is exclusively in the silica-containing layer. The support catalysts thus prepared can be used for the most diverse catalytic processes, for example hydrogenation, dehydrogenation, hydrogenolysis, oxidation, acetoxidation, polymerisation, isomerisation or cyclisation. In these catalytic reactions support catalysts thus prepared can be used not only when working in the bottom phase but also when working in the trickle phase or the gas phase. The trickle phase and the gas phase are preferable. The reactions can be carried out under atmospheric pressure, overpressure, or reduced pressure.

Catalytic hydrogenations are a preferable area of application for catalysts thus prepared. According to the composition of active ingredient the catalysts are particularly suitable for hydrogenating aliphatic multiple bonds, for example for selective hydrogenations, for the nuclear hydrogenation of aromatic systems or for hydrogenating certain constituents, for example nitro or carbonyl groups contained in aromatic systems. Certain compositions of active ingredient of the support catalysts thus prepared have a preferable application in catalytic hydrogenations, for example of substituted aromatics, wherein, depending on the combination of catalytically active substances as well as on other process parameters, such as temperature or pressure, either the aromatic system and/or the substituent can be hydrogenated.

A further important area of use is the acetoxidation of olefines, for example the formation of vinyl acetate from ethylene, acetic acid and oxygen using catalysts prepared according to the invention and containing palladium, gold and alkali metal acetate as catalytically active substances.

Catalysts prepared by the process according to the invention and containing the active substance palladium on $SiO_2$/steatite are preferably used for the catalytic hydrogenation of nitroaromatics, for example of nitrobenzene, nitrotoluene, dinitrobenzenes, dinitrotoluenes, trinitrotoluenes, nitrophenols and nitrochloroaromatics, to the corresponding aromatic amines. In the catalytic hydrogenation of nitro compounds, the gas phase reaction is preferable for mononitro compounds, while the liquid phase and, especially, the trickle phase is preferable for dinitro to trinitro compounds. Not only in the gas phase but also in the trickle phase the compound to be reduced is generally passed over a fixed catalyst. An excess of hydrogen is advantageously used. When working in the trickle phase the nitro compound to be reduced is usually diluted with the amino compound resulting in the reduction or with another diluent to such an extent that carrying out the reduction is free of hazards. The preferable reaction temperature in the trickle phase is within a range of 50° to 150° C., and the preferable pressure range is between 1 to 100 bar.

The hydrogenation in the gas phase is preferably carried out within a temperature range of 150° to 350° C. and under 1 to 10 bar.

A very general point to be made is that the application of products according to the invention as catalysts and catalyst supports is virtually not restricted. Virtually any catalytically active substance suitable for heterogeneous and/or homogeneous catalysis can be introduced, or produced, in the silica-containing layer of the products according to the invention, and the catalysts thus obtained can then be used in processes in which the activity of the particular catalytically active substances is known. The process conditions of such catalytic processes (quantities used, pressure, temperature, residence time and the like) vary in general when using catalysts according to the invention only to the extent possible on the basis of the improved activity and/or selectivity of the catalysts according to the invention. In many cases it is also possible simply to use catalysts according to the invention in lower active ingredient amounts than hitherto and obtain the same results as hitherto with unchanged processing conditions.

Examples which may be listed of the use of catalysts accessible according to the invention are:
(a) catalysts for hydrogenations and which contain noble metals and/or other metals, and which are, in particular, for example the following: For the hydrogenation of triple to double bonds catalysts which contain palladium or palladium with added amounts of lead, zinc, copper, chromium or amines and sulphur compounds. For the hydrogenation of diolefines to monoolefines catalysts which contain palladium. For the hydrogenation of monoolefines, for example in the hardening of fat, catalysts which contain Raney nickel. For the hydrogenation of unsaturated aldehydes to saturated aldehydes catalysts which contain platinum metals. For the hydrogenation of unsaturated nitriles to saturated nitriles catalysts which contain palladium. For the nuclear hydrogenation of aromatics catalysts which contain Raney nickel or rhodium. For the nuclear hydrogenation of phenols to cyclohexanols catalysts which contain palladium. For the hydrogenation of phenol to cyclohexanone catalysts which contain platinum. For the hydrogenation of aldehydes to alcohols catalysts which contain nickel. For the hydrogenation of unsaturated aldehydes to unsaturated alcohols catalysts which contain platinum, if appropriate with added amounts of zinc and/or iron. For the hydrogenation of carboxylic acids to alcohols catalysts which contain Raney cobalt. For the hydrogenation of carboxylic anhydrides to lactones or diols catalysts which contain nickel. For the hydrogenation of acid chlorides to aldehydes catalysts which contain palladium and sulphur-containing compounds. For the hydrogenation of nitriles to amines catalysts which contain either Raney cobalt or iron together with manganese and phosphorus-containing additives. For the hydrogenation of unsaturated nitriles to unsaturated amines catalysts which contain copper chromite and added amounts of barium compounds. For the hydrogenation of aldoximes to hydroxylamines catalysts which contain palladium of platinum. For the hydrogenation of aldoximes to amines catalysts which contain rhodium or platinum. For the conversion of ketones by means of hydrogen and ammonia to amines catalysts which contain cobalt and nickel. For the conversion of alcohols with ammonia and/or amines and hydrogen to amines catalysts which contain nickel. For the hydrogenation of nitro compounds to amines catalysts which contain copper chromite and barium compounds or palladium. For the ammonia synthesis catalysts which contain iron with added amounts of aluminium, potassium, magnesium and silicon compounds.
(b) Catalysts for dehydrogenations and oxidative dehydrogenation and which contain metal compounds, and which are, in particular, for example, the following: For the oxidative dehydrogenation of olefines to diolefines, in particular the conversion of butenes to butadienes, catalysts which contain magnesium ferrite with additives containing phosphorus and nickel or additives containing calcium nickel phosphate and, if appropriate, strontium and/or chromium or mixed molybdates (for example nickel cobalt iron bismuth molybdate and, if appropriate, additives containing phosphorus and potassium) or nickel calcium phosphate or mixed antimony tin oxides. For the dehydrogenation of hydrocarbons, in particular from ethylbenzene to styrene, catalysts which contain iron oxide and added amounts of chromium oxide and potassium compounds. For the dehydrogenation of linear hydrocarbons to aromatics, in particular from n-hexane to benzene, catalysts which contain chromium oxide and aluminum oxide with added amounts of alkali metal compounds. For the conversion of cyclohexanol to cyclohexanone, catalysts which contain zinc oxide and added amounts of alkali metal and alkaline earth metal compounds.
(c) Catalysts for hydration or dehydration and which contain phosphorus compounds and/or zeolites, and which are, in particular, for example as follows: For the hydration of olefines to alcohols, for example from ethylene to ethyl alcohol, catalysts which contain phosphoric acid and silicon dioxide. For the dehydration of secondary alcohols to olefines, in particular from β-hydroxyethylbenzene to styrene, catalysts which contain sodium metaphosphate and silicon dioxide or zeolites or aluminum oxide. For the conversion of carboxylic acids using ammonia with elimination of water to give nitriles, in particular from adipic acid to adipodinitrile, catalysts which contain phosphoric acid and silicon dioxide. For the dehydratitration of 1,4-butanediol to tetrahydrofuran, catalysts which contain acidic zeolites.

(d) Catalysts for reactions in the presence of carbon monoxide and which contain transition metals or transition metal compounds, and which are, in particular, for example the following: For the synthesis of alcohols, in particular of methanol, from carbon monoxide and hydrogen, catalysts which contain either zinc oxide or chromium oxide or copper and added amounts of zinc oxide, aluminium oxide, chromium oxide and/or alkali metal compounds. For the Fischer-Tropsch synthesis catalysts which contain iron and added amounts of alkali metal compounds, thorium oxide and magnesium oxide or catalysts which contain iron and aluminium oxide. For methanation catalysts which contain nickel and/or aluminium oxide or spinels or catalysts which contain ruthenium. For the conversion of carbon monoxide by means of steam catalysts which contain iron oxide and chromium oxide, or copper, zinc oxide and aluminium oxide or cobalt molybdenum sulphide and aluminium oxide. For steam reforming catalysts which contain nickel and alkali metal compounds.

(e) Catalysts for ammoxidation and which contain transition metals, and which are, in particular, for example the following: For the conversion of propylene to acrylonitrile, catalysts which contain vanadium antimony oxides or molybdenum bismuth iron cobalt (nickel) oxides and added amounts of potassium compounds and phosphorus compounds or of antimony iron oxides. For the conversion of o-xylene to phthalodinitrile catalysts which contain vanadium antimony oxides.

(f) Catalysts for oxidation reactions and which contain transition metals or transition metals oxides, and which are, for example, the following: For the conversion of olefines to unsaturated aldehydes, in particular from propylene to acrolein, and from i-butene to methacrolein, catalysts which contain copper oxide or molybdenum bismuth iron cobalt (nickel) phosphorus oxides or molybdenum niobium (tantalum) bismuth oxides, in each case with promoters if appropriate. For the conversion of unsaturated aldehydes to unsaturated acids, in particular from acrolein to acrylic acid and from methacrolein to methacrylic acid, catalysts which contain molybdenum vanadium tungsten oxides or molybdenum phosphorus niobium (tantalum) oxides, in each case with promoters if appropriate. For the conversion of $C_4$-hydrocarbons to maleic anhydride, catalysts which contain vanadium oxide and phosphorus oxide or molybdenum antimony vanadium oxides, in each case with promoters if appropriate. For oxyacetylations of olefines with the formation of esters of unsaturated alcohols, for example vinyl acetate and allyl acetate, catalysts which contain palladium and alkali metal acetates and, if appropriate, further metals or metal compounds (for example, gold, bismuth, cadmium or manganese). For the oxidation of ethylene to ethylene oxide, catalysts which contain silver and, if appropriate, added amounts of alkali metal compounds. For the oxidation of alcohols to aldehydes, in particular of methanol to formaldehyde, catalysts which contain silver or molybdenum iron oxides. For the oxidation of hydrocarbons to carboxylic acids or aldehydes, in particular from n-butene to acetic acid, catalysts which contain titanium vanadate. For the oxidation of aromatics to acid anhydrides or quinones, for example from benzene, naphthalene or o-xylene to phthalic anhydride and, if appropriate, naphthoquinone, catalysts which contain vanadium pentoxide together with added amounts of molybdenum oxide/phosphorus oxide or silicon dioxide/potassium pyrosulphate and for the oxidation of anthracene to anthraquinone catalysts which contain vanadium pentoxide.

(g) Catalysts for cleaning gas and which contain metals or metal oxides, and which are, in particular, for example the following: For the detoxification of gases from internal combustion engines, catalysts which contain platinum and ruthenium or platinum and palladium or platinum and rhodium, in each case with promoters if appropriate. For the removal of hydrogen sulphide by the Claus process, catalysts which contain activated alumina. For the removal of small amounts of chlorine or sulphur, catalysts which contain copper or zinc oxide. For the removal of small amounts of carbon monoxide or carbon dioxide, catalysts which contain nickel and magnesium aluminium spinell or ruthenium.

The examples which follow illustrate the present invention without restricting it in any way.

EXAMPLES

Survey

Part A: Description of starting materials

Part B: Description of methods for preparing products according to the invention Example
1 Spraying method-single coating
2 Spraying method-multiple coating
3 Thermal aftertreatment Part C: Comparison of catalysts according to the invention with the state of the art Example
1 Acetoxidation preparation of vinyl acetate
2 Oxidation of naphthalene
3 Hydrogenation of o-nitrotoluene Part D: Preparation examples of products according to the invention Examples 1-29

The percentage data, unless otherwise indicated, are percentages by weight.

Part A Description of starting materials
Materials 1 to 8 are various inorganic base materials, and Materials 9 to 17 are other starting materials for the experiments described in Parts B, C and D.

| Material No. |
| --- |

-continued

Part A Description of starting materials
Materials 1 to 8 are various inorganic base materials, and Materials 9 to 17 are other starting materials
for the experiments described in Parts B, C and D.

| | 1 Steatite | 2 Steatite | 3 Ash | 4 $SiO_2$ | 5 Steel | 6 Stainless steel | 7 Silicon carbide | 8 $Al_2O_3$ |
|---|---|---|---|---|---|---|---|---|
| Shape | Spheres 3.0-3.5 mm | Hollow cylinders 7 mm external diameter | Mill base 2.8-3.5 mm | Spheres 4.7-5.8 mm | Spheres 3.5 mm | Raschig rings 5 × 5 mm | Spheres 5 mm | Spheres 5 mm |
| Chemical composition [%] | | | | | | | | |
| $SiO_2$ | 62.15 | | 41.30 | 91.79 | | | 28.5 | <0.1 |
| $Al_2O_3$ | 4.28 | | 22.58 | 3.09 | | | 4.7 | >95 |
| $Fe_2O_3$ | 2.23 | | 16.38 | 0.58 | | | 0.3 | <0.1 |
| $Mn_2O_3$ | — | | 0.10 | — | | | — | |
| $TiO_2$ | 0.16 | | 0.92 | 0.45 | | | <0.01 | |
| CaO | — | | 7.72 | — | | | 0.2 | |
| MgO | 29.88 | | 3.80 | 0.13 | | | 0.1 | |
| $K_2O$ | 0.65 | | 3.50 | 0.77 | | | 0.1 | |
| $Na_2O$ | 0.93 | | 1.10 | — | | | 0.1 | 0.7 |
| Bulk density [kg/l] | 1.615 | 1.070 | 1.250 | 0.540-0.590 | 4.722 | 0.200 | 1.000 | 0.760 |
| Absorbency [g of $H_2O$/100 g of material] | — | — | — | 63 | — | — | 20.45 | 45 |
| BET surface area [$m^2$/g] | <1 | <1 | <0.1 | 150 | | | <0.3 | 350 |
| True density [g/cm$^3$] | | | | 2.732 | | | | |
| Apparent density [g/cm$^3$] | | | | 2.529 | | | | |
| Hg pore volume [mm$^3$/g] | | | | 15 | | | | |
| Total pore volume [mm$^3$/g] | | | 29 | 750 | | | | 450 |
| Porosity [%] | | | 7.4 | 64 | | | | |

Material No.

| 9. Silica sol | | 10. Silica | | 11. Waterglass | | 12. Kieselguhr | |
|---|---|---|---|---|---|---|---|
| Type | Bayer Kieselsol (silica sol) 300, 30% (commercial name) | Type | Ultrasil VN2 (commercial name) | Type | Potassium silicate in the form of an aqueous solution | Type | Purified and ignited in accordance with DAB (German Pharmacopoeia) Supplement B6 |
| $SiO_2$ content [%] | about 30 | Loss on ignition at 1000° C. [%] | 11 | | | | |
| $Na_2O$ content [%] | about 0.35 | of which moisture at 105° C. [%] | 6 | | | | |
| pH value | about 9.8 | $SiO_2$ content [%] | 87 | Density [g/cm$^3$] | 1.25 | $SiO_2$ [%] | >96 |
| Density [g/cm$^3$] | 1.2 | $Al_2O_3$ content [%] | 0.2 | $SiO_2$ [%] | 21 | pH value | 5-9 |
| Viscosity [mPa · sec] | 4-6 | $Na_2O$ content [%] | 0.8 | $K_2$ [%] | 8.1 | Fractions soluble in hydrochloric acid [%] | <1 |
| Specific surface area [$m^2$g] | about 280-320 | $SO_3$ content [%] | 0.5 | | | | |
| Particle size [nm] | 7-8 | $Fe_2O_3$ content [%] | <0.05 | | | Acid-soluble sulphate [%] | <0.02 |
| Ionic character | anionic | Specific density [g/cm$^3$] | 2.0 | | | Acid-soluble iron [%] | <0.04 |
| | | Compacted density [g/liter] | 200 | | | Loss on ignition (600° C.) [%] | <0.5 |
| | | pH value | 7 | | | Sieve residue >0.1 mm [%] | <2 |
| | | BET surface area [$m^2$/g] | 130 | | | | |
| | | Mean primary particle size [nm] | 28 | | | | |

Material No.

| 13. Vanadyl oxalate solution | 14. Activated carbon | | 15. Zeolite | | 16. Ion exchange material | |
|---|---|---|---|---|---|---|
| Aqueous solution containing 17.8% by weight of vanadyl oxalate, which corresponds to 10.4% by weight of $V_2O_5$, and having a density of 1.165 g/cm$^3$. | Bayer Carboraffin P (commercial name) | | Bayer Zeolite T-Pulver [zeolite T powder] (commercial name) (alkali metal alumosilicate of A type in the K form) | | Bayer Lewasorb SW 12 (commercial name) | |
| | Water at time of packing [% by weight] | <10 | | | Supply form | Na |
| | Fineness of grind [% by weight] | 20 75 μm | | | Grain form | Microgranules |
| | Vibrated density [kg] liter | about 0.3 | | | Basic structure | Polystyrene |
| | pH value | 5-7 | Pore width [nm] | 40 | Anchor group | Sulphonic acid |
| | Ash [% by weight] | 2.0-3.0 | Crystallite diameter [μm] | 2-10 | Grain size range [nm] | <0.1 (95% < 0.075) |
| | Molasses factor | about 1.0 | Bulk density [g/liter] | 350 | Bulk density [g/liter] | 700-800 |
| | | | pH value | 11 | Density [g/cm$^3$] | 1.28 |

Material No.
17. Alumina
   Identical to Material No. 8, but particle size <0.1 mm
Material No.
18. Polystyrene
   Granules, ellipsoid up to 3 mm; bulk density 682 g/l; softening temperature: 75° to 80° C.; commercial product from BASF under the name Polystyrol 143 c.
Material No.
19. Polymer alloy of polycarbonate and ABS
   Granules, extruded pieces up to 3 mm long; bulk density 640 g/l; softening temperature: 120° C.; commercial product from Bayer AG (see Bayer publication KL 46150 of June '81).
Material No.
20. Polyethylene
   Granules, ellipsoid up to 3.5 mm; bulk density 638 g/l; softening temperature: 90° C.; commercial product from Bayer AG (see Bayer publication KL 43570 of June '82).
Material No.
21. Cellulose ester
   Granules, extruded pieces up to 3.1 mm; bulk density 754 g/l; softening temperature: 60° to 100° C.; commercial product from Bayer AG (see Bayer publication kL 40001 to August '75).
Material No.
22. Glass fibre reinforced polyamide
   Granules, extruded pieces up to 3.5 mm long; bulk density 730 g/l; softening temperature: 255° C.; 50% glass fibre content; commercial product from Bayer AG (see Bayer publication kl 40360 of April '78).
Material No.
23. Polycarbonate
   Cylindrical granules up to 3 mm; bulk density 773 g/l; softening temperature up to 150° C.; commercial product from Bayer AG (see Bayer publication KL 46100 of August '79).
Material No.
24. Acrylonitrile-butadiene-styrene polymer (ABS polymer)
   Granules cut in the form of cubes, up to 3.5 mm; bulk density 673 g/l; softening temperature 102° C.; commercial product from Bayer AG (see Bayer publication KL 41654 of October '78).
Material No.
25. Glass fibre reinforced polyester
   Granules, extruded pieces up to 3.8 mm; bulk density 864 g/l; softening temperature up to 185° C.; 30% glass fibre content; commercial product from Bayer AG (see Bayer publication KL 41100 of June '81).

Part B: Description of methods for preparing products according to the invention using inorganic base materials Example 1: Spray method-single coating 1615 g of Material No. 1 (see Part A) are initially introduced into a 50 liter capacity, heatable coating drum and heated to 200° C. at a speed of 3 rpm.

Meanwhile, 443 g of silica sol, 133 g of Ultrasil VN2 and 133 g of kieselguhr (Materials Nos. 9, 10 and 12, see Part A) are stirred in a 3 liter container together with 1300 g of water to give a 20% strength by weight suspension. This suspension is discontinuously sprayed pneumatically with continuous stirring from a pressure vessel onto the continuously moving, hot, initially introduced inorganic base material at 200° C.

In this spraying step, the speed of the drum is increased within 15 minutes from 3 to 15 rpm and 300 g of suspension are sprayed on. As soon as the temperature of the moving material has dipped below 150° C., the spraying process is discontinued until 200° C. is again reached. The 1709 g of suspension still present are discontinuously applied within 45 minutes at a speed of 15 rpm. During this period, the moving material is maintained within the temperature range of 150°–200° C. After the application of the product is complete, the material is allowed to cool down to 40° C. while the drum is stationary and the drum is them emptied.

1765 g of a product containing 150 g of silica in the form of a layer having a mean density of 175 μm are obtained. The absorbency of this product is 4.2% while its bulk density is 1428 g/liter and it has a residual moisture content of <1%.

Example 2: Spraying method-multiple coating

Corresponding to Part B Example 1, 4038 g of Material No. 1 are sprayed with 4500 g of a mixture consisting of 1000 g of silica sol, 300 g of Ultrasil VN2, 300 g of kieselguhr (Materials Nos. 9, 10 and 12, see Part A) and 2900 g of water in the course of 2 hours. 400 g of the total mixture are applied within the first 15 minutes, and the rest is applied in the remaining 105 minutes.

4494 g of a product containing 456 g of silica in the form of a layer having a mean thickness of 150 μm are obtained.

In a further operating step, 2085 g of the product are sprayed again under the same conditions with 4500 g of the abovementioned mixture.

2498 g of product containing 413 g of silica in the form of a second layer are obtained. This product now has a total silica layer having a mean total thickness of 700 μm, a bulk density of 1180 g/liter and an absorbency of 11.9 ml/100 g.

Example 3: Thermal aftertreatment

The silica-containing product obtained in accordance with Part B Example 2 after a two-fold coating was subjected to a thermal aftertreatment, in which the product was thermally treated within a range of 200° to 1100° C. at various temperatures for 3 hours each, namely up to 500° C. in the coating drum by means of an acetylene oxygen burner and up to 1100° C. in an ignition furnace. The thermal aftertreatment produced the following BET surface areas as a function of the temperature.

| Temperature [°C.] | 200 | 300 | 400 | 500 | 600 | 700 | 800 | 900 | 1000 | 1100 |
|---|---|---|---|---|---|---|---|---|---|---|
| BET surface area relative to original coated spheres [m²/g] | 25.8 | 26.3 | 26.4 | 25.9 | 24.4 | 21.4 | 6.9 | 1.2 | 0.5 | 0.2 |

Identical results are obtained when the thermal aftertreatment is carried out in an ignition furnace from the start.

Part C: Comparison of catalysts according to the invention with the state of the art

Example 1: Acetoxidation, preparation of vinyl acetate (a) Comparative catalyst German Patent Specification 1,668,088 describes a catalyst for synthesising vinyl acetate. Replication of the examples of this patent specification shows that the catalyst support contains an interior zone which contains a palladium/gold alloy, whereas the alkali metal acetate is distributed throughout the entire support. The catalyst produces 245 g of vinyl acetate per hour and per liter of catalyst at 140° C. The catalyst is prepared according to Example 1 of German Patent Specification 1,668,088 by treating the support simultaneously with a solution of palladium salts and gold salts and a solution which contains compounds capable of reaction on the catalyst support with the palladium salts and the gold salts to form water-insoluble palladium and gold compounds, then converting the water-insoluble palladium and gold compounds by treatment with reducing agents into the noble metals and then washing out the water-soluble compounds. Then alkali metal acetate (potassium acetate) is applied by impregnation, so that the prepared catalyst contains about 30 g of potassium acetate/liter.

(b) Catalyst according to the invention 1180 g=1000 ml of the product prepared in Part B Example 2 by two-fold coating are impregnated with 140 ml of a solution containing 3.3 g of Pd in the form of $Na_2PdCl_4$ and 1.5 g of Au in the form of $HAuCl_4$. The volume of the impregnating solution corresponds to the absorbency of the product. To reduce the noble metals the product thus impregnated is coated with 5% strength hydrazine hydrate solution and left to stand for 4 hours to complete the reduction. The product is then washed with water, and adhering water is then removed by drying. 1168.7 g of a catalyst which, commensurate with its absorbency, is further impregnated with 135 ml of an aqueous solution containing 15 g of potassium acetate, are thus obtained. After a drying process at 115° C., 1180 g=970 ml of a catalyst which can be used for preparing vinyl acetate are obtained.

(c) Preparation of vinyl acetate 900 ml of the catalyst prepared in accordance with (b) are packed into a 2 m long reaction tube of 25 mm internal diameter under the conditions described in German Patent Specification 1,668,088, Example 5. 77 mols of ethylene, 19 mols of gaseous acetic acid and 5.8 mols of oxygen are passed per hour over the catalyst at 140° C. and under a pressure of 8 bar. 357 g of vinyl acetate were formed per hour and per liter of catalyst.

Example 2: Oxidation of naphthalene (a) Comparative catalyst

Catalyst A of Example 1 of German Offenlegungsschrift 2,453,232 was prepared.

In this preparation, a vanadyl sulphate solution obtained from $V_2O_5$, $H_2SO_4$ and $SO_2$ is mixed with finely pulverulent silica prepared from potassium silicate solution and sulphuric acid. The paste thus obtained is introduced into perforated plates having a thickness of 5 mm and a diamter of 5 mm and dried for 2 hours at 50° C. The shaped articles thus obtained are then dried at 125° C. and then heat-treated for 12 hours at 425° C. This produced Catalyst 1.

(b) Catalyst according to the invention

Corresponding to Part B of Example 1, 500 g of silicon carbide (see Part A, Material No. 7), 253 g of silica sol, 76 g of Ultrasil VN2, 76 g of kieselguhr (Materials Nos. 9, 10 and 23, see Part A), 106 g of 97% strength sulphuric acid, 301 g of an aqueous vanadyl oxalate solution (corresponding to 31.8 g of vanadium pentoxide) and 183 g of potassium sulphate are mixed with 215 g of water to give a 46% strength suspension. This suspension is applied to the silicon carbide in a manner corresponding to Part B Example 1.

965 g of a coated product are obtained with a layer thickness of 1000 μm. This produced Catalyst 2.

(c) Naphthalene oxidation

Naphthalene was reacted with oxygen in the presence of Catalyst 1 and, separately thereof, in the presence of Catalyst 2, both reactions being carried out under the conditions described in German Offenlegungsschrift 2,453,232. The reactions were carried out in a 3 m long steel reaction tube having an internal diameter of 30 mm and being heated by means of a salt bath. A gas mixture of 94% of nitrogen and 6% of oxygen was passed at a rate of 4 $Nm^3/h$ into the reactor, first at room temperature under a pressure of 6 bar. This gas mixture was heated to 200° C. and then additionally enriched with water at a rate of 300 ml/hour. The mixture was then heated to 350° C., and the catalyst was treated for 24 hours at this temperature and under 6 bar with the nitrogen/oxygen/steam mixture. The temperature was then reduced to 320° C. and naphthalene was passed in the form of a gas at a rate of 690 g/hour over the catalyst in addition to the mixture containing nitrogen, oxygen and steam. The temperature was then increased to 360° C. at a rate of 6° C./hour. After the catalyst had run for 500 hours the following results were obtained:

| Catalyst | Space-time yield (g of naphthoquinone per liter of catalyst and per hour) | Space-time yield (g of phthalic anhydride per liter of catalyst and per hour) | Ratio by weight of naphthoquinone to phthalic anhydride |
|---|---|---|---|
| 1 | 39.1 | 50.7 | 0.77:1 |
| 2 | 45.8 | 46.4 | 0.98:1 |

Catalyst 2 thus produced considerably improved yields in respect of the naphthoquinone space-time yield and in respect of the ratio of naphthoquinone to phthalic anhydride.

Example 3: Hydrogenation of o-nitrotoluene (a) Comparative catalyst

German Patent Specification 1,545,297 describes the preparation of a hydrogenation catalyst. Example 4 was repeated in such a way that a catalyst containing 5 g of Pd per liter of Li spinel was obtained. This produced Catalyst 1.

(b) Catalyst according to the invention

Corresponding to Example 24 (see Part D), 50 ml=65 g of a support (prepared in a manner corresponding to Part D of Example 15) are impregnated with 5.3 ml of a solution which contains 1.67 g of $Na_2PdCl_4$ (corresponding to 0.25 g of palladium), 20 ml of a 10% by weight strength hydrazine solution are added to convert the palladium into the elemental state, and the support is washed with demineralised water until neutral and chloride-free and then dried to constant weight at 110° C. in a stream of warm air.

50 ml of a catalyst which contains 5 g of Pd per liter of catalyst are obtained. This produced Catalyst 2.

(c) Hydrogenation of o-nitrotoluene

The hydrogenation of o-nitrotoluene is carried out under atmospheric pressure in a shaking flask with a small built-in basket to receive the catalyst. In each case 10 ml of catalyst, 5 g of o-nitrotoluene and 35 ml of methanol are introduced into the flask at 50° C. and under 0.1 bar hydrogen pressure. The quantity measured was the time of hydrogen absorption.

| Catalyst | Hydrogenation time [min] | Conversion of o-nitrotoluene [%] |
|---|---|---|
| 1 | 270 | 98.9 |
| 2 | 220 | 99.0 |

Catalyst 2 produced improved values in respect of hydrogenation time and the degree of conversion of o-nitrotoluene.

Part D: Preparation examples of products according to the invention

Examples 1-5

A very wide variety of support materials are coated in accordance with part B of Example 1

| | Example No. | | | | | |
|---|---|---|---|---|---|---|
| | 1* | 2 | 3 | 4 | 5 | 5a |
| Starting materials No. of Part A | | | | | | |
| Inorganic base material No. | 4 | 2 | 5 | 6 | 3 | 2 |
| Amount used [g] | 577 | 2180 | 340 | 200 | 4725 | 1070 |
| Silica sol No. | 9 | 9 | 9 | 9 | 9 | 9 |
| Amount used [g] | 290 | 1667 | 444 | 288 | 1081 | 676 |
| Kieselguhr No. | 12 | 12 | — | 12 | 12 | — |
| Amount used [g] | 87 | 250 | — | 87 | 324 | — |
| Ultrasil VN 2 No. | 10 | — | — | 10 | 10 | — |
| Amount used [g] | 87 | — | — | 87 | 324 | — |
| Potassium waterglass No. | | | 11 | | | — |
| Amount used [g] | — | — | 319 | — | — | — |
| Vanadyl oxalate solution No. | 13 | — | 13 | 13 | 13 | |
| Amount used [g] | 344 | — | — | 344 | 1290 | 274 |
| Potassium sulfate [g] | 209 | — | — | 209 | 784 | 163 |
| Sulphuric acid 97% [g] | 121 | — | — | 121 | 455 | 92 |
| Water [g] | 146 | — | 237 | 146 | 830 | — |
| Yield [g] product | 985 | — | 468 | 495 | 6505 | 1400 |
| An increase in weight relative to the weight of inorganic base material used | | | | | | |
| [g] | 71 | 480 | 128 | 295 | 1780 | 428 |
| [%] | 66 | 22 | 38 | 148 | 37.7 | 40 |
| mean layer thickness in μm | n.d. | 420 | n.d. | n.d. | 791** | n.d. |

-continued

| | Example No. | | | | | |
|---|---|---|---|---|---|---|
| | 1* | 2 | 3 | 4 | 5 | 5a |

Remarks
*The operating temperature during the application deviated from Part B Example 1 and was 200-230° C.
**The layer thickness varies between 2,025 μm and 455 μm. A series of measurements gave the mean layer thickness at 791 μm. Such pronounced fluctuations in the layer thicknesses do not occur in geometrically regularly shaped inorganic base materials, such as, for example, in the case of spheres.
n.d. means not determined.
The products of Examples 1, 4, 5 and 5a are catalysts for the oxidation of naphthalene. The products of Examples 2 and 3 are precursors for preparing catalysts (see Example 24).

Examples 6-12

Layers of various mean thicknesses are prepared in accordance with Part B, Example 1

| Experimental conditions | Example No. | | | | | | |
|---|---|---|---|---|---|---|---|
| | 6 | 7 | 8 | 9 | 10 | 11 | 12 |
| Starting materials No. from Part A | | | | | | | |
| Inorganic base material No. | 1 | 1 | 1 | 1 | 1 | 1 | 1 |
| Amount used [g] | 1625 | 1625 | 1625 | 1600 | 1615 | 1600 | 1600 |
| Silica sol No. | 9 | 9 | 9 | 9 | 9 | — | — |
| Amount used [g] | 41 | 112 | 722 | 1000 | 555 | — | — |
| Kieselguhr No. | 12 | 12 | 12 | | | — | — |
| Amount used [g] | 12 | 34 | 217 | — | — | — | — |
| Potassium waterglass No. | | | | | | 11 | 11 |
| Amount used [g] | — | — | — | — | — | 1587 | 793 |
| Ultrasil No. | 10 | 10 | 10 | 10 | | — | — |
| Amount used [g] | 12 | 34 | 217 | 100 | | — | — |
| Alumina No. | | | | | 17 | | |
| Amount used [g] | — | — | — | — | 333 | — | — |
| Zeolite No. | | | | | | 15 | 15 |
| Amount used [g] | — | — | — | — | — | 190 | 375 |
| Activated carbon No. | | | | 14 | | | |
| Amount used [g] | — | — | — | 400 | — | — | — |
| Vanadyl oxalate solution No. | 13 | 13 | 13 | | | | |
| Amount used [g] | 49 | 133 | 862 | — | — | — | — |
| Potassium sulfate [g] | 30 | 81 | 523 | — | — | — | — |
| Sulphuric acid 100% [g] | 17 | 47 | 304 | | | | |
| Water [g] | 282 | 768 | 4953 | 2500 | 1611 | 722 | 1331 |
| Yield [g] product | 1690 | 1823 | 2800 | 1651 | 1954 | 2300 | 2102 |
| An increase in weight relative to the weight of inorganic base material used | | | | | | | |
| [g] | 65 | 198 | 1175 | 51 | 339 | 700 | 502 |
| [%] | 4 | 12 | 72 | 3 | 21 | 44 | 31 |
| mean layer thickness in μm | 50 | 150 | 650 | 50 | 350 | n.d. | n.d. |

Remarks
The products of Examples 6-8 are catalysts suitable for the oxidation of naphthalene.
The products of Examples 9-12 are catalyst support materials. If, in accordance with Part C Example 3b, these materials are coated with palladium in such a way that they contain 1.5% of palladium, catalysts are obtained which are suitable for the hydrogenation of o-nitrotoluene by the method described in Part C Example 3c.
n.d. means not determined.

Tables 13-19

Silica layers having differing physical properties are prepared in accordance with Part B, Example 1.

| Experimental conditions | Example No. | | | | | | |
|---|---|---|---|---|---|---|---|
| | 13 | 14 | 15 | 16 | 17 | 18 | 19 |
| Starting materials No. from Part A | | | | | | | |
| Inorganic base material No. | 1 | 1 | 1 | 1 | 1 | 1 | 1 |
| Amount used [g] | 1615 | 1615 | 1615 | 1615 | 1615 | 1600 | 1600 |
| Silica sol No. | 9 | 9 | 9 | 9 | 9 | 9 | 9 |
| Amount used [g] | 666 | 887 | 887 | 447 | 1333 | 417 | 833 |
| Kieselguhr No. | 12 | 12 | — | 12 | — | — | — |
| Amount used [g] | 100 | 134 | — | 133 | — | — | — |
| Potassium waterglass No. | — | — | — | — | — | 11 | 11 |
| Amount used [g] | — | — | — | — | — | 1190 | 595 |
| Ultrasil No. | 10 | — | 10 | 10 | — | 10 | 10 |
| Amount used [g] | 100 | — | 134 | 133 | — | 125 | 125 |
| Water [g] | 1133 | 979 | 979 | 1287 | 667 | 768 | 947 |
| Yield [g] product | 1793 | 1906 | 1954 | 1765 | 1986 | 2192 | 1824 |
| An increase in weight relative to the weight of inorganic base material used | | | | | | | |
| [g] | 178 | 291 | 339 | 150 | 371 | 592 | 224 |
| [%] | 11.5 | 18 | 21 | 9.3 | 23 | 37 | 14 |
| Mean layer thickness [μm] | 95 | 140 | 335 | 180 | 185 | n.d. | n.d. |
| True density [g/cm$^3$/g]* | 2.589 | 2.576 | 2.549 | 2.606 | 2.556 | 2.366 | 2.552 |
| Apparent density [g/cm$^3$]* | 2.210 | 2.297 | 2.027 | 2.281 | 2.273 | 1.748 | 2.389 |
| Total pore volume [mm$^3$/g]* | 66 | 47 | 101 | 54 | 49 | 149 | 27 |
| BET surface area [m$^2$/g]* | 11.6 | 12.8 | 24.9 | 9.2 | 22.4 | <0.1 | <0.1 |
| Mean pore diameter [Å]* | 230 | 150 | 160 | 230 | 90 | n.d. | n.d. |
| Porosity [%] | 14.5 | 10.8 | 20.5 | 12.5 | 11.1 | 26.1 | 6.4 |

*These values are relative to the total product, that is inorganic base material plus silica layer.
The products of Examples 13-19 are catalyst support materials. If, in accordance with Part C Example 3b, these materials are coated with palladium in such a way that they contain 1.5% of palladium, catalysts are obtained which are suitable for the hydrogenation of o-nitrotoluene by the method described in Part C Example 3c.
n.d. means not determined

Examples 20 and 20a

Procedure in accordance with Part B Example 1; preparation of catalysts with the addition of porosity-producing agents.

| Experimental conditions | Example No. | |
|---|---|---|
| | 20 | 20a |
| Starting materials No. from Part A | | |
| Inorganic base material No. | 1 | 1 |
| Amount used [g] | 1615 | 16150 |
| Silica sol No. | 9 | 9 |
| Amount used [g] | 288 | 3335 |
| Kieselguhr No. | 12 | — |
| Amount used [g] | 86 | — |
| Potassium waterglass No. | — | — |
| Amount used [g] | — | — |
| Ultrasil No. | 10 | — |
| Amount used [g] | 86 | — |
| Vanadyl oxalate solution No. | 13 | 13 |
| Amount used [g] | 344 | 4498 |
| Potassium sulphate [g] | 209 | 2668 |
| Sulphuric acid 97% [g] | 121 | 1511 |
| Water [g] | 816 | 3200 |
| Oxalic acid dihydrate [g] | 125 | — |
| Graphite [g] | — | 2400 |
| Yield [g] product | 2095 | 23305 |
| An increase in weight relative to the weight of inorganic base material used | | |
| [g] | 480 | 7155 |
| [%] | 30 | 44 |

The products thus obtained are catalysts suitable for the oxidation of naphthalene. They were activated by passing over 1 m$^3$ of air per liter of catalyst for 8 hours at 400° C.

The graphite used in Example 20a is a so-called fine powder graphite obtained from Messrs. Brockhues, Niederwalluf (Federal Republic of Germany). According to its specification, this graphite has a particle size of 95% below 0.1 mm, a carbon content of 85% by weight and an ash content of 15% by weight.

Examples 21-23

Products are prepared by two-fold coating in accordance with Part B, Example 2

| Experimental conditions | Example No. | | | |
|---|---|---|---|---|
| | 21 | 22 | 23a | 23b* |
| Starting materials No. from Part A | | | | |
| Inorganic base material No. | 1 | Final product of Example 21 | 8 | Final product of 23a |
| Amount used [g] | 4585 | 3290 | 820 | 730 |
| Silica sol No. | 9 | 9 | — | 9 |
| Amount used [g] | 1000 | 1081 | — | 333 |
| Kieselguhr No. | — | 12 | — | — |
| Amount used [g] | — | 324 | — | — |
| Potassium waterglass No. | 11 | — | 11 | 11 |
| Amount used [g] | 2857 | — | 1250 | 952 |
| Ultrasil No. | 10 | 10 | — | — |
| Amount used [g] | 300 | 324 | — | — |
| Ion exchange material | | | | 16 |
| Amount used [g] | | | | 100 |
| Vanadyl oxalate solution No. | — | 13 | — | — |
| Amount used [g] | — | 1290 | — | — |
| Potassium sulphate [g] | — | 784 | — | — |
| Sulphuric acid 100% [g] | — | 455 | — | — |
| Water [g] | 1843 | 829 | 500 | 524 |
| Yield [g] product | 6025 | 4743 | 1060 | 1260 |
| An increase in weight relative to the weight of inorganic base material used | | | | |
| [g] | 1440 | 1453 | 240 | 530 |

-continued

| Experimental conditions | Example No. | | | |
|---|---|---|---|---|
| | 21 | 22 | 23a | 23b* |
| [%] | 31 | 44 | 29 | 73 |

Remarks
The product of Example 22 is a catalyst suitable for the oxidation of naphthalene. The product of Example 23b is a catalyst support material. If this is coated with 1.5% of palladium (see Part C Example 3b), a catalyst is obtained which is suitable for the hydrogenation of o-nitrotoluene.
*The coating was effected at 130–150° C. because of instability of the ion exchange material at higher temperatures.

Examples 24–29

Various products according to the invention and coated with a silica-containing layer are coated with various active ingredients.

Preparation and properties of the starting products:

| | Preparation | Absorbency [g of water/ 100 g of starting material] | Bulk density [g/ liter of starting material] |
|---|---|---|---|
| for Example 24 | In accordance with Part D Example 15 | 8.2 | 1296 |
| for Examples 25 to 29 | In accordance with Part B Example 1 | 4.2 | 1428 |

Example 24

50 ml = 65 g of the starting product indicated above are impregnated with 5.3 ml of a solution containing 6.9 g of $Na_2PdCl_4$ solution (corresponding to 1 g of palladium), 20 ml of a 10% by weight strength hydrazine solution are added to convert the palladium into the elemental state, and the support is washed with demineralised water until neutral and chloride-free and then dried to constant weight at 110° C. in a stream of warm air.

50 ml of a catalyst which contains 20 g of Pd per liter of catalyst are obtained. This catalyst is suitable for the hydrogenation of o-nitrotoluene.

Example 25

100 ml = 143 g of the starting product indicated above are impregnated with 6.0 ml of a solution containing 1.645 g of ruthenium nitrate hydrate (corresponding to 0.5 g of Ru), dried and heat-treated at 400° C. The ruthenium oxide thus deposited is reduced to the metal by treatment with hydrogen at an elevated temperature.

100 ml of the catalyst which contains 5 g of Ru per liter of catalyst are obtained. This catalyst is suitable for the hydrogenation of o-nitrotoluene.

Example 26

100 ml = 143 g of the starting product indicated above are impregnated with 6.0 ml of a solution containing 7.5 g of $NiCl_2.6H_2O$ (corresponding to 1.85 g of Ni) and dried to constant weight in vacuo at 80° C.

100 ml of a catalyst which contains 18.5 g of Ni in the form of nickel chloride per liter of catalyst are obtained.

Example 27

100 ml = 143 g of the starting product indicated above are impregnated with 6.0 ml of a solution containing 10.0 g of $(Cu(NO_3)_2.3H_2O$ (corresponding to 2.6 g of Cu) and dried to constant weight in vacuo at 80° C.

100 ml of a catalyst which contains 26 g of Cu, in the form of copper nitrate, per liter of catalyst are obtained.

Example 28

100 ml = 143 g of the starting product indicated above are impregnated with 6.0 ml of a solution containing 10.0 g of $Co(NO_3)_2.6H_2O$ (corresponding to 2 g of Co) and dried to constant weight in vacuo at 80° C.

100 ml of a catalyst which contains 20 g of Co in the form of cobalt nitrate, per liter of catalyst are obtained.

Example 29

100 ml = 143 g of the starting product indicated above are impregnated with 6.0 ml of a solution containing 6.0 g of $FeCl_3.6H_2O$ (corresponding to 1.24 g of Fe) and dried to constant weight in vacuo at 80° C.

100 ml of a catalyst which contains 1.24 g of Fe in the form of iron chloride per liter of catalyst are obtained.

The products of Examples 26–29 are catalysts yet to be activated by hydrogen treatment. The catalysts thus activated can be used for the hydrogenation of o-nitrotoluene

Part E: Description of preparation methods for products according to the invention using organic base materials

Example 30

341 g of polystyrene (material No. 18, see Part A) are initially introduced into a 50 liter capacity, heatable coating drum, and heated to 70° C. at a speed of 4 rpm. In the meantime, 2,500 g of silica sol and 250 g of potassium waterglass (materials 9 and 11, see Part A) are added to each other in a 3 liter vessel with stirring. This mixture is then pneumatically sprayed with continuous stirring from a pressure vessel onto the continuously agitated, initi-ally introduced polystyrene which at the start of the application was at 70° C. As soon as the temperature of the agitated material drops below 60° C., the spray process is interrupted until the temperature has returned to 70° C. This process is carried out four times. This is followed by four applications within a temperature range of 80° to 70° C., six in a temperature range of 100° to 85° C., six in a temperature range of 120° to 100° C., and the remaining ones within a temperature range of 150° to 100° C.

After the application is complete, the product is allowed to cool down to 40° C. at a drum speed of 1 rpm, and the drum is emptied.

763 g are obtained of a product which contains 422 g of silica in the coating. The absorbency of the product is 12.48% at a bulk density of 785 g/l and at a residual moisture content of <1%.

The product thus obtained is heat-treated in a muffle furnace to remove the polystyrene, the temperature being raised to 700° C. at a rate of 50° C./h. The starting product is kept at this temperature until the entire organic content has been driven off. This is recognised by the attainment of constant weight.

417 g of product are obtained, which correspond to 98.8% of theory.

Examples 31 to 37

A very wide variety of support materials are coated as in Example 30 (Part E).

|  | Example No. | | | | | | |
| --- | --- | --- | --- | --- | --- | --- | --- |
|  | 31 | 32 | 33 | 34 | 35 | 36 | 37 |
| Organic base material (No., see Part A) | 19 | 20 | 21 | 22 | 23 | 24 | 25 |
| Amount used [g] | 463 | 608 | 390 | 730 | 386 | 778 | 864 |
| Silica sol (No., see Part A) | 9 | 9 | 9 | 9 | 9 | 9 | 9 |
| Amount used [g] | 600 | 417 | 500 | 833 | 500 | 1,399 | 1,555 |
| Silica (No., see Part A) | 10 | 10 | 10 | 10 | 10 | 10 | 10 |
| Amount used [g] | 180 | 208 | 155 | 250 | 150 | 420 | 467 |
| Waterglass (No., see Part A) | 11 | 11 | 11 | 11 | 11 | 11 | 11 |
| Amount used [g] | 1,714 | 1,984 | 1,400 | 2,381 | 1,428 | 2,000 | 2,222 |
| Water [g] | 360 | 250 | 300 | 1,536 | 300 | 900 | 1,000 |
| Yield [g of product] | 1,111 | 1,338 | 780 | 1,644 | 938 | 1,634 | 1,970 |
| Increase in weight relative to the weight of organic base material used | | | | | | | |
| [g] | 648 | 730 | 390 | 914 | 551 | 856 | 1,106 |
| [%] | 140 | 120 | 100 | 125 | 142 | 110 | 128 |
| Heat treatment of the coated organic support | | | | | | | |
| maximum temperature [°C.] | 700 | 700 | 700 | 700 | 700 | 700 | 700 |
| decrease in weight [%] | 35 | 40 | 45 | 24 | 43 | 50 | 30 |

Example 38

393 g of material obtained as in Example 30 but without removal of the polystyrene are sprayed in the course of 4 hours as in Example 1 of Part B with 1,489 g of a mixture consisting of 337 g of vanadyl oxalate solution (material No. 13, see Part A), 113 g of 98% strength sulphuric acid, 201 g of potassium sulphate and 838 g of silica sol (material No. 9, see Part A).

725 g of product are obtained, which corresponds to a weight increase relative to the amount of starting material used of 85% or 332 g. The product thus obtained was heat-treated at 400° C. for 17 hours, this temperature being reached over a period of 8 hours.

This produced 507 g, corresponding to a 30% weight decrease, as final product, which can be used as catalyst for the oxidation of naphthalene.

We claim:

1. A process for preparing silica-containing shaped articles, comprising applying a mass selected from the group consisting of silica sol, a mixture containing water, silica sol and waterglass and a mixture containing water and waterglass to a base material while the temperature of the base material is, at the start of the application of the silica sol or of the mixture, below the softening point of the base material and, as the application of the silica sol or of the mixture proceeds, above the boiling temperature of water, and the silica sol or the mixture is added in such a way that the water evaporates rapidly and the water content of the base material is always less than 5% by weight, whereby to surround the base material with a porous silica-containing layer.

2. A process according to claim 1, wherein the base material is composed of an inorganic material and at least at the surface of the base material, has an absorbency of less than 10 g of water per 100 g and a BET surface area of less than 5 m²/g.

3. A process according to claim 2, wherein the temperature of the base material is within a range of 105° to 800° C. during the application of the silica sol or of the mixture.

4. A process according to claim 1, wherein the base material is composed of an organic material and the temperature of the base material at the start of the application of the silica sol or of the mixture is kept below its softening point, as the application of silica sol or mixture proceeds the process is carried out at temperatures within a range of 105° to 220° C., and the base material is then removed by heating to temperatures within the range of 200° to 1,300° C.

5. A process according to claim 1, wherein silica sol or a mixture is applied until a silica-containing layer having a thickness within a range of 10 to 3000 um has formed.

6. A process according to claim 1, wherein catalytically active substances or precursors thereof are applied together with silica sol or with the mixture containing silica or a mixture is first applied which produces a silica-containing layer free of catalytically active substances or precursors thereof and solutions or suspensions of catalytically active substances or precursors thereof are then introduced into the layer.

7. A silica-containing shaped article comprising a base material surrounded by a firmly adhering layer consisting essentially of porous silica and a catalytically active substance or precursor thereof, said base layer having an absorbency less than 10 g of water per 100 g, a BET surface area below 5 m²/g and a thickness of 10 to 3,000 μm.

8. A silica-containing shaped article according to claim 7, wherein the base material comprises magnesium silicate.

9. A silica-containing shaped article according to claim 7, which further comprises a second layer disposed between the base material and said first layer.

10. A silica-containing shaped article according to claim 7, wherein the base material is a solid polymeric material selected from the group consisting of polystyrenes, polycarbonates, polyolefins, cellulose, cellulose derivatives, polyurethanes, polyacrylonitriles, acrylonitrilestyrene-butadiene copolymers, polyesters, polyvinyl chlorides, polyfluoroethylenes, polyfluoroethylene derivatives, polyamides, epoxy resins and polycondensates.

11. A silica-containing shaped article according to claim 7, wherein the base material has an absorbency of less than 5 g of water per 100 g.

12. A silica-containing shaped article according to claim 7, wherein the thickness of the layer is 20 to 2,000 μm.

13. A silica-containing shaped article according to claim 7, wherein the thickness of the layer is 1 to 100 μm.

14. A process according to claim 1, which further comprises applying finely pulverulent and/or water-insoluble silica with said silica sol and/or mixtures.

15. A process according to claim 1, wherein the base material is a solid polymeric material selected from the group consisting of polystyrenes, polycarbonates, polyolefins, cellulose, cellulose derivatives, polyurethanes, polyacrylonitriles, acrylonitrilestyrene-butadiene copolymers, polyesters, polyvinyl chlorides, polyfluoroethylenes, polyfluoroethylene derivatives, polyamides, epoxy resins and polycondensates.

16. A process according to claim 1, wherein said silica sol contains 15 to 45% by weight $SiO_2$, below 0.5% by weight of Na$_2$O, has a pH of 3.4 to 10, a density of 1.09 to 1.33 g/cm$^3$ and a particle size of 7 to 30 μm.

17. A process according to claim 1, wherein said mass is selected from the group consisting of (a) 10 to 80% by weight of silica sol and an amount to add up to 100% by weight of finely pulverulent, water-insoluble silica, (b) 10 to 60% by weight of waterglass and an amount to add up to 100% by weight of finely pulverulent, water-insoluble silica, and (c) 10 to 90% by weight of silica sol and waterglass, the waterglass content being at most 60% by weight of the mixture, and an amount to add up to 100% by weight of finely pulverulent, water-insoluble silica, in each of (a), (b), (c) the % by weight calculated and relative to anhydrous SiO$_2$.

18. A process according to claim 1, wherein the mass is relative to all silica constituents therein and calculated as anhydrous SiO$_2$, 30 to 95% by weight, of water.

19. A process according to claim 1, wherein said base material is an organic material and said temperature is 105° to 300° C.

20. A process according to claim 1, wherein said base material is an inorganic material charge and the base material is heated to 200° to 250° C. and then sprayed with said mass until the temperature of the charge falls to 105° to 150° C. and then sprayed again.

21. A silica-containing shaped article produced by a process comprising applying a mass selected from the group consisting of silica sol, a mixture containing water, silica sol and waterglass, a mixture containing water and waterglass and a mixture containing water and silica sol, said silica sol containing finely pulverulent water-insoluble silica having a primary particle size in a range of 1 to 200 nm and an agglomerate size withing a range of 0.5 to 100 μm, to a base material having an absorbency of less than 10 g of water per 100 g and a BET surface area of less than 5 m$^2$/g, while the temperature of the base material is, at the start of the application of the silica sol or the mixtures, below the softening point of the base material and, as the application of the silica sol or of the mixtures proceed, above the boiling temperature of water, and adding the silica sol or the mixtures in such a way that the water evaporates rapidly and the water content of the base material is always less than 5% by weight.

22. A process according to claim 14, wherein the silica has a primary particle size of 1 to 200 nm an an agglomerate size of 0.5 to 100 μm.

23. A process according to claim 14, wherein the silica is kieselguhr.

24. A process according to claim 1, wherein the silica sol or one of said mixtures is applied at a temperature above the boiling point of water.

25. A process according to claim 1, which further comprises applying a porosity-forming agent with said silica sol and/or mixtures, said porosity-forming agent selected from the group consisting of activated carbon, carbon black, graphite ammonium salts, aliphatic alcohols of the empirical formula $C_nH_{2n+2}O$, aliphatic dihydroxy, trihydroxy and polyhydroxy compounds, aliphatic carboxylic acids of the empirical formula $C_nH_{2n}O_2$, aliphatic dicarboxylic acids of the empirical formula $C_nH_{2n-2}O_4$, higher aliphatic carboxylic acids and sugars and readily and completely decomposable polymers.

26. A process according to claim 25, wherein the porosity-forming agent is selected from the group consisting of ammonium carbonate, ammonium hydrogencarbonate, ammonium nitrate, ammonium acetate, ammonium formate, ammonium oxalate, ethylene glycol, glycerol, sugar alcohols, acetic acid, propionic acid, oxalic acid, sodium acetate, malonic acid, ascorbic acid, tartaric acid, citric acid, glucose, sucrose, starch, cellulose and polystyrene.

* * * * *

UNITED STATES PATENT AND TRADEMARK OFFICE
CERTIFICATE OF CORRECTION

PATENT NO. : 4,764,498
DATED : Aug. 16, 1988
INVENTOR(S) : Wissner et al.

It is certified that error appears in the above-identified patent and that said Letters Patent is hereby corrected as shown below:

| | |
|---|---|
| Col. 7, line 15 | Correct spelling of --organic-- |
| Col. 10, line 66 | Delete "container" and substitute --contained-- |
| Col. 19, last line of item 9 | Insert --Colour clear-- |
| Col. 21, line 33 | Delete "kl" and substitute --KL-- |
| Col. 23, line 64 | Correct spelling of --diameter-- |

Signed and Sealed this

Twenty-fifth Day of April, 1989

Attest:

DONALD J. QUIGG

*Attesting Officer*  *Commissioner of Patents and Trademarks*